US009292655B2

(12) United States Patent
Arazi et al.

(10) Patent No.: US 9,292,655 B2
(45) Date of Patent: Mar. 22, 2016

(54) METHOD AND COMPUTING SYSTEM FOR PROVIDING AN INTERFACE BETWEEN AN IMAGING SYSTEM AND A REPORTING SYSTEM (71) Applicant: McKesson Financial Holdings, Hamilton (BM)

(72) Inventors: Ohad Arazi, Vancouver (CA); Sheri Morita, Vancouver (CA)

(73) Assignee: McKesson Financial Holdings, Hamilton (BM)

( * ) Notice: Subject to any disclaimer, the term of this patent is extended or adjusted under 35 U.S.C. 154(b) by 241 days.

(21) Appl. No.: 13/953,216

(22) Filed: Jul. 29, 2013

(65) Prior Publication Data
US 2015/0032471 A1    Jan. 29, 2015

(51) Int. Cl.
G06K 9/00        (2006.01)
G06F 19/00       (2011.01)

(52) U.S. Cl.
CPC .......... *G06F 19/321* (2013.01); *G06F 19/3487* (2013.01)

(58) Field of Classification Search
None
See application file for complete search history.

(56) References Cited

U.S. PATENT DOCUMENTS

| | | | | |
|---|---|---|---|---|
| 2006/0101016 A1* | 5/2006 | Uehara | ................ | G06F 19/321 |
| 2008/0126982 A1* | 5/2008 | Sadikali | ................ | G06F 19/321 |
| | | | | 715/810 |
| 2008/0232702 A1* | 9/2008 | Kimoto | ................ | A61B 1/041 |
| | | | | 382/232 |
| 2009/0051691 A1* | 2/2009 | Kimoto | ............. | A61B 1/00009 |
| | | | | 345/473 |
| 2009/0175417 A1* | 7/2009 | Sasano | ................ | G06F 19/321 |
| | | | | 378/98.5 |
| 2010/0114597 A1* | 5/2010 | Shreiber | ............... | G06F 19/321 |
| | | | | 705/2 |
| 2010/0131873 A1* | 5/2010 | Mejia et al. | ................... | 715/764 |
| 2011/0161108 A1* | 6/2011 | Miller | .................... | G06Q 10/10 |
| | | | | 705/3 |
| 2012/0035963 A1* | 2/2012 | Qian | ................... | G06F 19/3487 |
| | | | | 705/3 |
| 2012/0221347 A1* | 8/2012 | Reiner | ................ | G06F 19/321 |
| | | | | 705/2 |
| 2012/0254794 A1* | 10/2012 | Bocirnea | ....................... | 715/809 |
| 2013/0039552 A1* | 2/2013 | Becker | ................ | G06F 19/321 |
| | | | | 382/128 |
| 2013/0151286 A1* | 6/2013 | Kablotsky | ........... | G06F 19/3418 |
| | | | | 705/3 |
| 2013/0251233 A1* | 9/2013 | Yang | ..................... | G06T 7/0012 |
| | | | | 382/132 |
| 2013/0325510 A1* | 12/2013 | Vendrell | ............... | G06F 19/321 |
| | | | | 705/3 |
| 2014/0006926 A1* | 1/2014 | Yeluri | ................... | G06F 19/321 |
| | | | | 715/234 |
| 2014/0013199 A1* | 1/2014 | Buurman | ...................... | 715/226 |
| 2014/0140591 A1* | 5/2014 | Arazi | ............................ | 382/128 |
| 2014/0143719 A1* | 5/2014 | Arazi | .................... | G06F 19/324 |
| | | | | 715/810 |

* cited by examiner

*Primary Examiner* — Aaron W Carter
(74) *Attorney, Agent, or Firm* — Alston & Bird LLP (57) ABSTRACT A method, apparatus and computer program product are disclosed to provide an interface between an imaging system for presenting medical images acquired by various modalities and a reporting system for generating and presenting reports, such as reports relating to the medical images. In the context of a method, the method may include participating in a transfer of information relating to a context of one or more images presented by the imaging system so as to cause a reporting template to be restructured based upon the context of one or more images presented by the imaging system. The method also includes causing an action to be taken in one of the imaging system or the reporting system based upon data provided by another of the imaging system or the reporting system.

20 Claims, 7 Drawing Sheets

METHOD AND COMPUTING SYSTEM FOR PROVIDING AN INTERFACE BETWEEN AN IMAGING SYSTEM AND A REPORTING SYSTEM

TECHNOLOGICAL FIELD

An example embodiment of the present invention relates generally to the presentation and review of medical images and, more particularly, to an interface between an imaging system for presenting medical images of a patient and a reporting system for generating and presenting reports relating to the patient, such as reports relating to the medical images of a patient.

BACKGROUND

Medical imaging often includes creating images of regions of the human body for clinical purposes such as examination, diagnosis and/or treatment. These images may be acquired by a number of different imaging modalities including, for example, ultrasound (US), magnetic resonance (MR), positron emission tomography (PET), computed tomography (CT), mammograms (MG), digital radiology (DR), computed radiology (CR) or the like. In a number of example medical imaging workflows, such as in the case of a picture archiving and communication system (PACS), an image study for a patient may include one or more acquired images of the patient. A radiologist or other health care provider may review the images for diagnostic or other purposes.

A report is oftentimes generated, such as by a radiologist or other health care provider, based upon the images of a patient. A report generally includes information identifying the patient, the image study and the like as well as content describing the author's interpretation of the images. The reports are generally comprised of free-form text and may be created in various manners. For example, reports may be dictated and then transcribed, either manually or based upon voice recognition. To facilitate consistency, reports may be generated utilizing structured templates and macros that define various sections to be populated with free-form text.

The reporting systems utilized by radiologists and other health care providers to generate reports are not only diverse, but are typically distinct from the imaging systems. Moreover, the textual format of the reports stands in stark contrast to the visual nature of the images generated and presented by an imaging system that are the basis for the report. As a result of the differences between the textual format of the reports and the visual format of the images and the differences between the reporting and imaging systems, the efficiency with which a report may be generated may be less than as desired and the richness of the data available in the report may be somewhat limited.

By way of example, a majority of radiology reports are generated in the United States utilizing voice recognition systems. In order to generate a report utilizing a voice recognition system, a typical workflow involves the radiologist selecting an image study from a PACS worklist and then opening a PACS viewer. The voice recognition system may also be launched, either automatically or in response to actuation by the radiologist. The PACS may then transfer basic identifiers to the voice recognition system including, for example, a patient identifier, a study identifier and a user identifier. The PACS viewer may load the images of the image study in a predefined configuration in which the images are considered to "hang". The predefined configuration in which the images "hang" may be defined by a display protocol (DP). Display protocols generally arrange the images on the display in accordance with a predetermined pattern that has been determined to be appropriate for the type of study. The predetermined pattern defined by the display protocol may depend upon the modality type, the procedure type, the body region and/or the specific preferences of the radiologist.

Once launched, the voice recognition system may load a report template having a predefined order which is specific to the reporting application and the site. However, the ordering of the report template does not necessarily match the arrangement of the images as defined by the display protocol. As such, the radiologist may be required to flip back and forth between the various images presented by the imaging system to review the body regions or organs in the order defined by the report template. While reviewing the images, the radiologist may dictate a variety of information relating to the image study including, for example, measurements recorded on the images and/or the comparison studies that were viewed including their date, orientation, etc. The resulting report may then be stored for subsequent review, such as by a primary care physician, a surgeon or other health care provider.

BRIEF SUMMARY

A method, apparatus and computer program product are provided in accordance with one embodiment of the present invention in order to provide an interface between an imaging system for presenting medical images acquired by various modalities and a reporting system for generating and presenting reports, such as reports relating to the medical images. As such, the method, apparatus, and computer program product of an example embodiment may facilitate the generation of reports in an efficient manner. Additionally, the method, apparatus and computer program product of an example embodiment may permit the medical images and the associated reports to be accessed in an efficient and intuitive manner, thereby allowing a radiologist or other healthcare provider who is reviewing the medical images to consider the associated reports without diverting their attention from the review of the medical images to locate the reports.

In one embodiment, a method of providing an interface between an imaging system and a reporting system is provided. The method includes participating in a transfer of information relating to a context of one or more images presented by the imaging system to cause a reporting template to be restructured based upon the context of one or more images presented by the imaging system. For example, the information relating to a context of one or more images may include a display protocol relating to an order in which the one or more images are presented by the imaging system. The method also includes causing, with a processor, an action to be taken in one of the imaging system or the reporting system based upon data provided by another of the imaging system or the reporting system.

With respect to a reporting system, the reporting system may participate in the transfer of information by receiving information relating to the context of one or more images presented by the imaging system. In this embodiment, the method may also include restructuring the reporting template from a reporting template having a first order to a reporting template having a second order based upon the context of one or more images presented by the imaging system.

Various actions may be taken in accordance with embodiments of the present invention. For example, causing an action to be taken may include causing a section of the reporting template to be auto-populated with a measurement captured with the imaging system. Additionally or alternatively, causing an action to be taken may include causing an indication of one or more comparison studies maintained by the imaging system to be included within a section of the reporting template. In another embodiment, causing an action to be taken may include causing an actuable identifier to an image maintained by the imaging system to be included within a section of the reporting template. Further, causing an action to be taken may also or alternatively include causing an annotation to be associated with an image maintained by the imaging system.

In another embodiment, a computing system for providing an interface between an imaging system and a reporting system is provided. The computing system includes processing circuitry configured to participate in a transfer of information relating to a context of one or more images presented by the imaging system to cause a reporting template to be restructured based upon the context of one or more images presented by the imaging system. For example, the information relating to a context of one or more images may include a display protocol relating to an order in which the one or more images are presented by the imaging system. The processing circuitry is also configured to cause an action to be taken in one of the imaging system or the reporting system based upon data provided by another of the imaging system or the reporting system.

With respect to a reporting system, the reporting system may participate in the transfer of information by receiving information relating to the context of one or more images presented by the imaging system. In this embodiment, the processing circuitry may also be configured to restructure the reporting template from a reporting template having a first order to a reporting template having a second order based upon the context of one or more images presented by the imaging system.

Various actions may be taken in accordance with embodiments of the present invention. For example, the processing circuitry may be configured to cause an action to be taken by causing a section of the reporting template to be auto-populated with a measurement captured with the imaging system. Additionally or alternatively, the processing circuitry may be configured to cause an action to be taken by causing an indication of one or more comparison studies maintained by the imaging system to be included within a section of the reporting template. In another embodiment, the processing circuitry may be configured to cause an action to be taken by causing an actuable identifier to an image maintained by the imaging system to be included within a section of the reporting template. Further, the processing circuitry may be configured to cause an action to be taken by causing an annotation to be associated with an image maintained by the imaging system.

In a further embodiment, a computer program product for providing an interface between an imaging system and a reporting system is provided. The computer program product includes at least one non-transitory computer-readable storage medium having computer-executable program code instructions stored therein. The computer-executable program code instructions include program code instructions for participating in a transfer of information relating to a context of one or more images presented by the imaging system to cause a reporting template to be restructured based upon the context of one or more images presented by the imaging system. For example, the information relating to a context of one or more images may include a display protocol relating to an order in which the one or more images are presented by the imaging system. The computer-executable program code instructions also include program code instructions for causing an action to be taken in one of the imaging system or the reporting system based upon data provided by another of the imaging system or the reporting system.

With respect to a reporting system, the reporting system may participate in the transfer of information by receiving information relating to the context of one or more images presented by the imaging system. In this embodiment, the computer-executable program code instructions may also include program code instructions for restructuring the reporting template from a reporting template having a first order to a reporting template having a second order based upon the context of one or more images presented by the imaging system.

Various actions may be taken in accordance with embodiments of the present invention. For example, the program code instructions for causing an action to be taken may include program code instructions for causing a section of the reporting template to be auto-populated with a measurement captured with the imaging system. Additionally or alternatively, the program code instructions for causing an action to be taken may include program code instructions for causing an indication of one or more comparison studies maintained by the imaging system to be included within a section of the reporting template. In another embodiment, the program code instructions for causing an action to be taken may include program code instructions for causing an actuable identifier to an image maintained by the imaging system to be included within a section of the reporting template. Further, the program code instructions for causing an action to be taken may also or alternatively include program code instructions for causing an annotation to be associated with an image maintained by the imaging system.

In yet another embodiment, an apparatus for providing an interface between an imaging system and a reporting system is provided. The apparatus includes means for participating in a transfer of information relating to a context of one or more images presented by the imaging system to cause a reporting template to be restructured based upon the context of one or more images presented by the imaging system. The apparatus also includes means for causing an action to be taken in one of the imaging system or the reporting system based upon data provided by another of the imaging system or the reporting system.

BRIEF DESCRIPTION OF THE DRAWINGS

Having thus described certain example embodiments of the invention in general terms, reference will now be made to the accompanying drawings, which are not necessarily drawn to scale, and wherein:

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Further, the apparatus and method of example embodiments of the present invention will be primarily described in conjunction with medical-imaging applications. It should be understood, however, that the apparatus and method may be utilized in conjunction with a variety of other applications, both in the medical industry and outside the medical industry. Like numbers refer to like elements throughout.

A method, apparatus and computer program product are provided in accordance with an example embodiment of the present invention in order to permit a report to be generated by a radiologist or other health care provider (hereinafter generically referred to as a "radiologist") who is reviewing one or more medical images of a patient in an efficient manner. In this regard, the report may include one or more findings related to a respective risk profile of a patient. The method, apparatus and computer program product of an example embodiment may also be configured to permit the report to be generated in such a manner as to facilitate the subsequent review of the report and/or the corresponding images, thereby potentially improving the review of the medical images and/or increasing the efficiency with which those medical images are reviewed.

Figure 1:
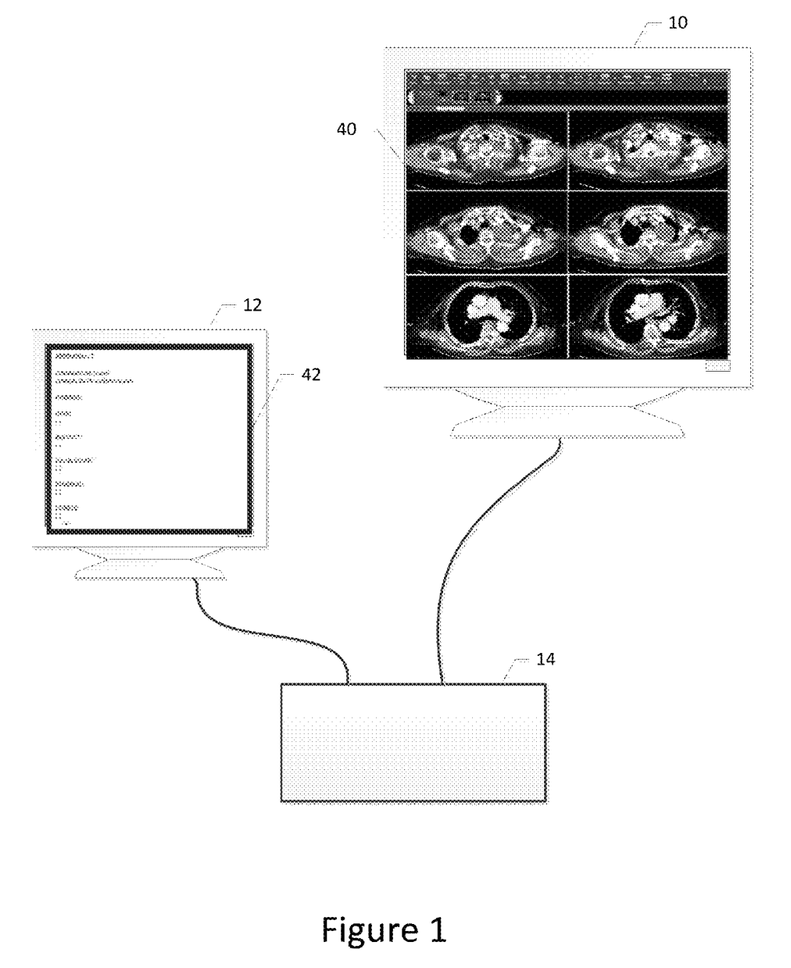
FIG. 1 is a schematic representation of an imaging system and a reporting system that may be configured in accordance with an example embodiment of the present invention.

The method, apparatus and computer program product of an example embodiment of the present invention may be embodied by a computing system. In one embodiment, the computing system may be embodied by a diagnostic imaging system, such as a PACS. Alternatively, the computing system may be embodied by a reporting system, such as the Powerscribe® voice recognition system that is provided by Nuance Communications, Inc. Further, the computing system may be embodied by a combination of a diagnostic imaging system and a reporting system. However, other types of computing systems, such as one or more computer workstations, personal computers or the like, may embody the method, apparatus and computer program product of an embodiment of the present invention in order to provide an interface, such as a bi-directional interface, between the imaging system and the reporting system. In the embodiment of FIG. 1, for example, both an imaging system 10 and a reporting system 12 may include a display, a user interface (not shown), e.g., keyboard, mouse, touch screen, etc., and a computing device that may include a processing circuit and one or more memory devices. In the illustrated embodiment, the imaging system and the reporting system are both supported by the same computing device 14, such as a server. However, the imaging system and the reporting system may include distinct computing devices that are in communication with one another, such as either in a wireless or wireline manner.

Figure 2:
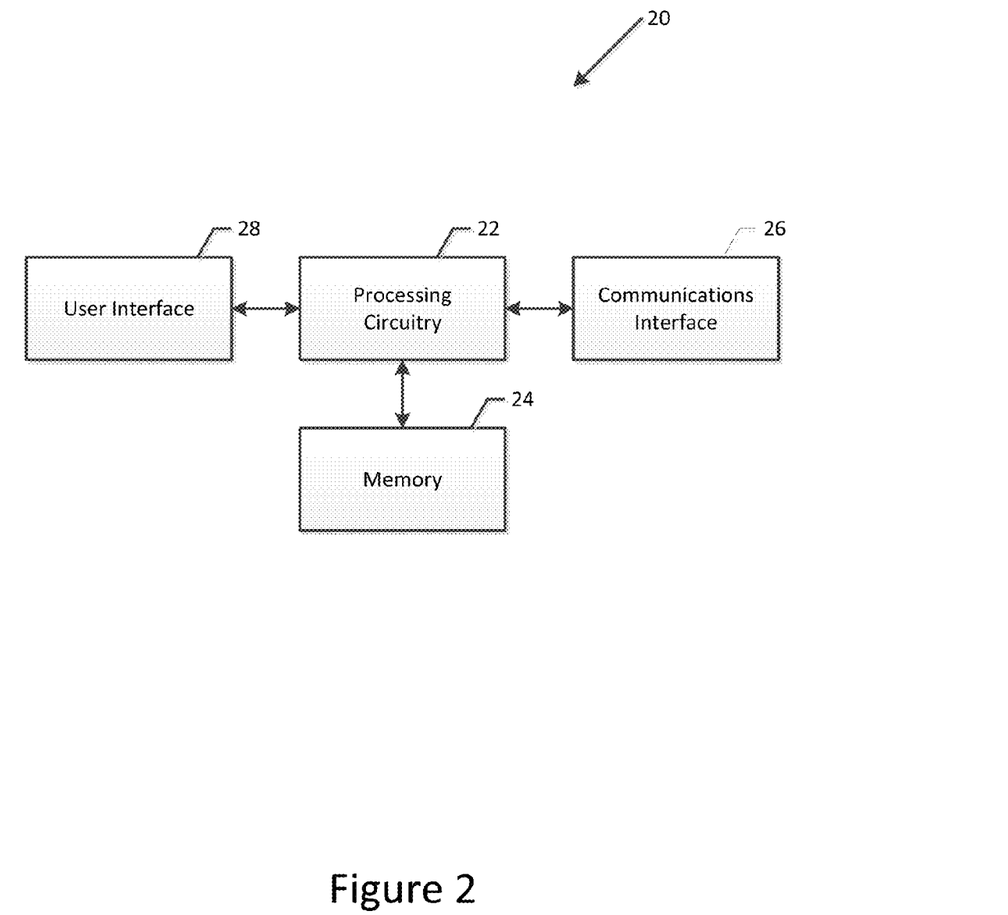
FIG. 2 is a block diagram of an apparatus that may be embodied by or otherwise associated with an imaging system and/or a reporting system and that may be specifically configured in accordance with an example embodiment of the present invention.

Regardless of the instantiation of the computing system, the computing system may include or otherwise be associated with an apparatus 20 that may, in turn, be specifically configured in order to perform one or more operations in associated with an embodiment of the present invention. As shown in FIG. 2, for example, the apparatus of one embodiment may include various means for performing the various functions described herein. These means may include, for example, one or more of a processing circuitry 22, memory 24, communication interface 26 and/or user interface 28 for performing the various functions herein described. The means of the apparatus as described herein may be embodied as, for example, circuitry, hardware elements (e.g., a suitably programmed processor, combinational logic circuit, and/or the like), a computer program product comprising computer-readable program instructions (e.g., software or firmware) stored on a computer-readable medium (e.g. memory) that is executable by a suitably configured processing device (e.g., the processing circuitry), or some combination thereof.

The processing circuitry 22 may, for example, be embodied as various means including one or more microprocessors, one or more coprocessors, one or more multi-core processors, one or more controllers, one or more computers, various other processing elements including integrated circuits such as, for example, an ASIC (application specific integrated circuit) or FPGA (field programmable gate array), or some combination thereof. Accordingly, although illustrated in FIG. 2 as a single processing circuitry, in some embodiments the processor may comprise a plurality of processing circuits. The plurality of processing circuits may be embodied on a single computing device or may be distributed across a plurality of computing devices collectively configured to function as the apparatus. The plurality of processing circuits may be in operative communication with each other and may be collectively configured to perform one or more functionalities of the apparatus as described herein. In some example embodiments, the processing circuitry is configured to execute instructions stored in the memory 24 or otherwise accessible to the processing circuitry. These instructions, when executed by the processing circuitry, may cause the apparatus 20 to perform one or more of the functionalities of the apparatus as described herein. As such, whether configured by hardware or software methods, or by a combination thereof, the processing circuitry may comprise an entity capable of performing operations according to embodiments of the present invention while configured accordingly. Thus, for example, when the processing circuitry is embodied as an ASIC, FPGA or the like, the processing circuitry may comprise specifically configured hardware for conducting one or more operations described herein. Alternatively, as another example, when the processing circuitry is embodied as an executor of instructions, such as may be stored in the memory, the instructions may specifically configure the processing circuitry to perform one or more algorithms and operations described herein.

The memory 24 may include, for example, volatile and/or non-volatile memory. Although illustrated in FIG. 2 as a single memory, the memory may comprise a plurality of memories. The plurality of memories may be embodied on a single computing device or distributed across a plurality of computing devices. The memory may comprise, for example, a hard disk, random access memory, cache memory, flash memory, an optical disc (e.g., a compact disc read only memory (CD-ROM), digital versatile disc read only memory (DVD-ROM), or the like), circuitry configured to store information, or some combination thereof. In this regard, the memory may comprise any non-transitory computer readable storage medium. The memory may be configured to store information, data, applications, instructions, or the like for enabling the apparatus 20 to carry out various functions in accordance with example embodiments of the present invention. For example, in some example embodiments, the memory is configured to buffer input data for processing by the processing circuitry 22. Additionally or alternatively, in some example embodiments, the memory is configured to store program instructions for execution by the processing device.

The communication interface 26 may be embodied as any device or means embodied in circuitry, hardware, a computer program product comprising computer readable program instructions stored on a computer readable medium (e.g., the memory 24) and executed by the processing circuitry 22, or a combination thereof that is configured to receive and/or transmit data from/to another device, such as, for example, a data storage device or other archive for storing electronic medical records. In some example embodiments, the communication interface is at least partially embodied as or otherwise controlled by the processing circuitry. In this regard, the communication interface may be in communication with the processing circuitry, such as via a bus. The communication interface may provide for communications via a wireline connection or may support wireless communications in which the communication interface may include, for example, an antenna, a transmitter, a receiver, a transceiver and/or supporting hardware or software for enabling communications. The communication interface may be configured to receive and/or transmit data using any protocol that may be used for communications between computing devices. As an example, the communication interface may be configured to receive and/or transmit data using any protocol and/or communications technology that may be used for communicating with the other devices. The communication interface may additionally be in communication with the memory and/or user interface 28, such as via a bus.

The user interface 28 may be in communication with the processing circuitry 22 to receive an indication of a user input and/or to provide an audible, visual, mechanical, or other output to a user. As such, the user interface may include, for example, a keyboard, a mouse, a joystick, a display, a touch screen display, a microphone, a speaker, and/or other input/output mechanisms. The user interface may be in communication with the memory 24 and/or communication interface 26, such as via a bus.

Figure 3:
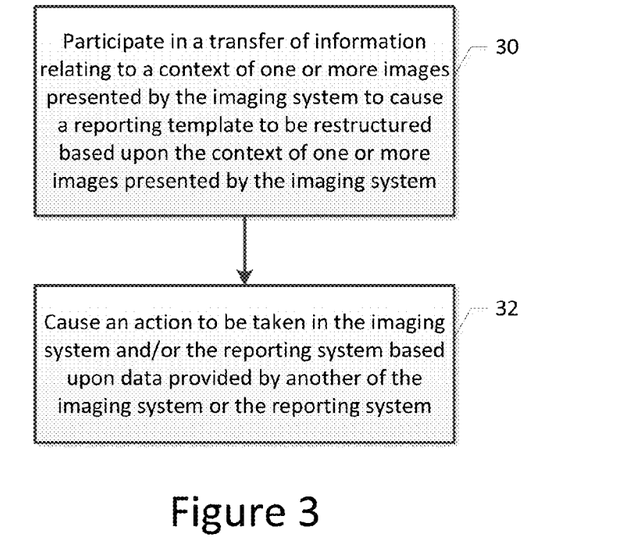
FIG. 3 is a flow chart illustrating operations performed, such as by the apparatus of FIG. 2, in accordance with an example embodiment of the present invention.

Referring now to FIG. 3, the operations performed, such as by the apparatus 20 of FIG. 2, in accordance with an example embodiment of the present invention are illustrated. In this regard, the apparatus may include means, such as the processing circuitry 22, for participating in a transfer of information relating to a context of one or more images presented by the imaging system 10 to cause a reporting template utilized by the reporting system 12 to be restructured based upon the context of one or more images presented by the imaging system. See block 30 of FIG. 3. From the perspective of the imaging system, the imaging system may participate in the transfer of information relating to the context of one or more images that it presents by causing information relating to the context of one or more images to be transmitted or otherwise provided to a reporting system. Conversely, a reporting system may participate in a transfer of information relating to the contest of one or more images presented by the imaging system by receiving information, typically from the imaging system or an intermediary, relating to the context of one or more images presented by the imaging system, as will be described below in conjunction with FIG. 4.

Various types of information relating to the context of one or more images presented by the imaging system may be transferred. For example, the information relating to the context of one or more images presented by the imaging system may include the display protocol or at least information relating to the display protocol that defines the order or sequence in which the images, such as the images of an image study, are presented. The information relating to the context of one or more images presented by the imaging system may also include, for example, information defining one or more comparison studies that are presented, such as along with the image study of interest.

As shown in block 32 of FIG. 3, the apparatus 20 may also include means, such as the processing circuitry 22, for causing an action to be taken in the imaging system 10 and/or the reporting system 12 based upon data provided by the other one of the imaging system or the reporting system. As will be described below, a variety of different actions may be taken by the imaging system based upon data provided by the reporting system and/or a variety of actions may be taken by the reporting system based upon data provided by the imaging system.

Figure 5:
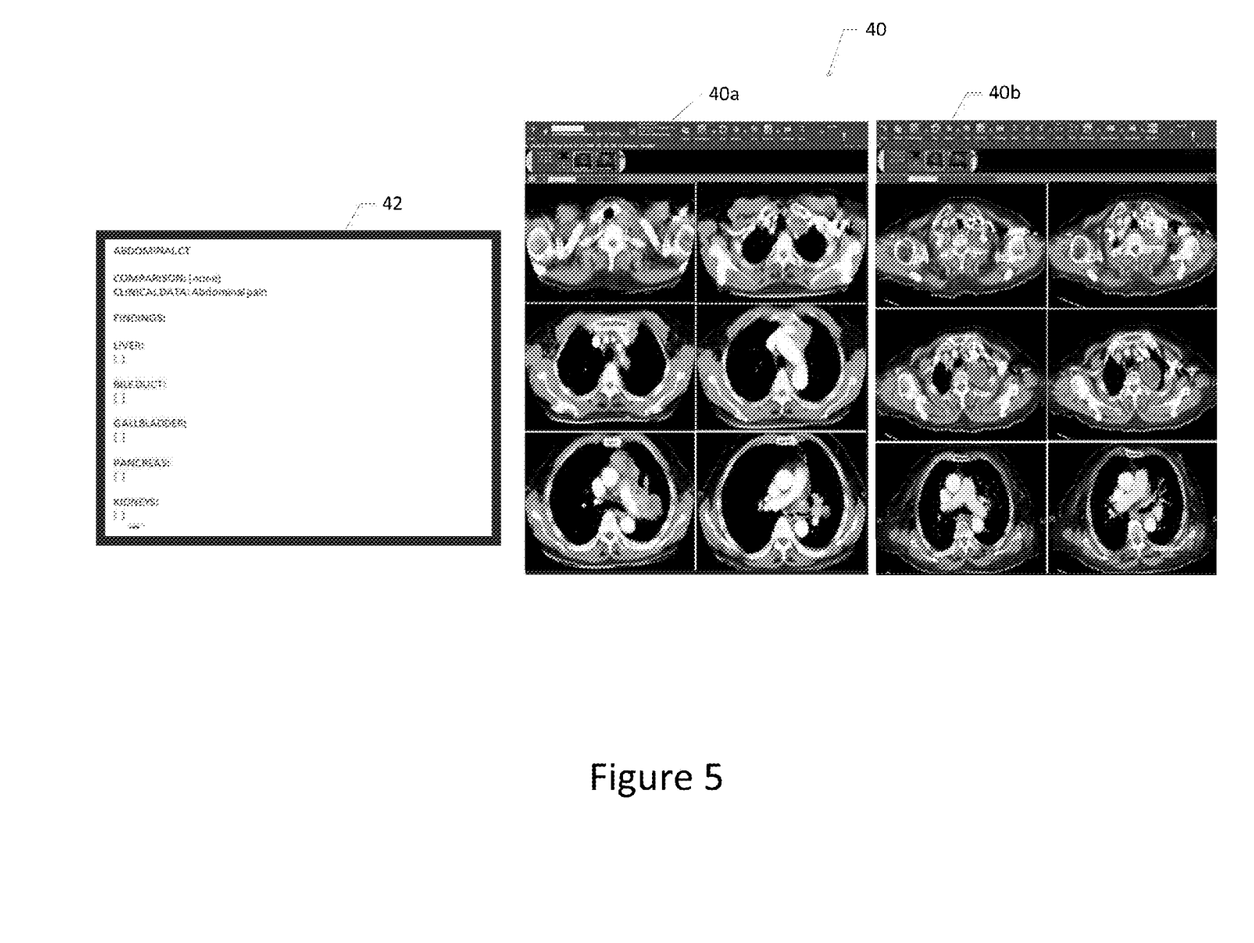
FIG. 5 depicts a plurality of images presented by an imaging system and a report template presented by a reporting system and structured in accordance with the context of the images in accordance with an example embodiment of the present invention.

By way of example, however, an action to be taken by the reporting system 12 based upon data provided by the imaging system 10 may include the restructuring of a reporting template so as to be reordered based upon the context of one or more images presented by the imaging system. In this regard, the reporting system may restructure the reporting template such that the plurality of sections of the reporting template which may correspond, for example, to regions of the body, organs or the like, are otherwise arranged in the same order as the images of the regions of the body, the organs or the like are presented by the imaging system. As shown in FIG. 5, for example, the imaging system may present a plurality of images 40, such as upon a display, that may be arranged in accordance with a display protocol. In addition to the image study 40*a* that has been selected by a radiologist or other health care provider, the images presented by the imaging system may also include images from one or more comparison studies 40*b*. The reporting system of this embodiment may also present a reporting template 42, such as upon a display. In this embodiment, the reporting template may have been restructured based upon the context of the one or more images presented by the imaging system. As such, the sections of the reporting template, such as the sections relating to the liver, bile duct, gall bladder, pancreas and kidneys, may be restructured so as to be ordered in the same manner in which the images presented by the imaging system that relate to the corresponding regions or organs of the body are displayed in accordance with the display protocol. As such, the radiologist or other health care practitioner can more efficiently enter their findings or other information relating to each of the regions or organs of the body since the sections of the reporting template have been restructured to follow the same order in which the images are presented by the imaging system.

Figure 4:
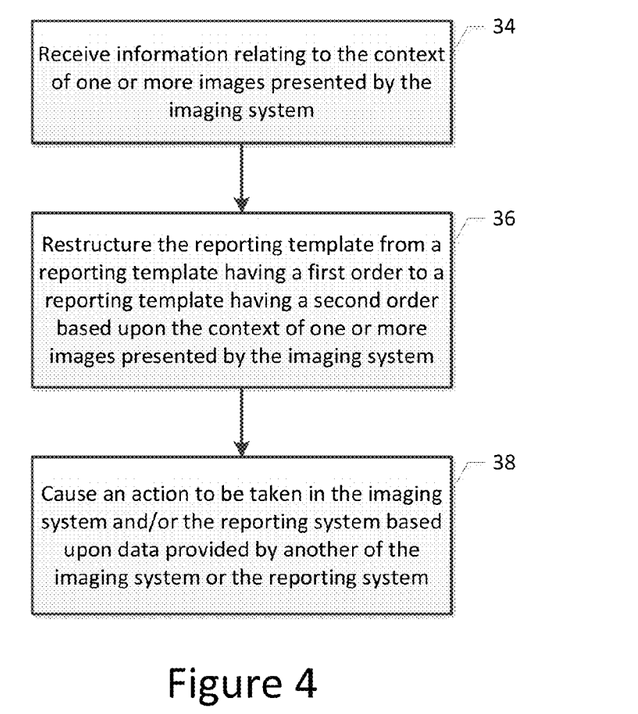
FIG. 4 is a flow chart illustrating operations performed, such as by the apparatus of FIG. 1 embodied by or otherwise associated with a reporting system, in accordance with an example embodiment of the present invention.

By way of further example, FIG. 4 depicts the operations performed by a reporting system 12 in accordance with an example embodiment of the present invention. As shown in block 34 of FIG. 4, the apparatus 20 embodied by or otherwise associated with a reporting system may include means, such as the processing circuitry 22, the communication interface 26 or the like, for participating in the transfer of information relating to the context of one or more images presented by the imaging system 10 by receiving information relating to the context of one or more images presented by the imaging system. As described above, various types of information may be received relating to the context of one or images presented by the imaging system including, for example, information defining the order in which the images are presented by the imaging system, such as the display protocol or information relating to the display protocol. In addition or alternatively, the information relating to the context of one or more images presented by the imaging system may include information regarding one or more comparison studies that are also presented by the imaging system.

As shown in block 36 of FIG. 4, the apparatus 20 embodied by or otherwise associated with the reporting system 12 may also include means, such as the processing circuitry 22, for restructuring the reporting template from a reporting template having a first order to a reporting template having a second order based upon the context of one or more images presented by the imaging system 10. In this regard, a reporting template may be initially structured to have a first order. The first order of the reporting template may be predefined and, in one instance is predefined for a site, e.g., hospital or other health care facility, a practice, e.g., a primary care, orthopedic or surgical practice, or the like. For example, the first order may be predefined in order to increase the efficiency with which the report may be reviewed as the report will have a familiar organization so as to enable a health care provider to quickly locate the sections of the report that are of interest. Based upon the context of one or more images presented by the imaging system, however, the order of the sections of the reporting template relating to various regions or organs of the body may be modified, at least during the generation of the report, so as to match or otherwise be correlated to the order or sequence in which the images of the corresponding regions or organs of the body are presented by the imaging system. As such, the resulting order of the sections of the reporting template may have a second order, different from the first order, at least during the generation of the report that more closely follows the sequence of the images presented by the imaging system. Following generation of the report, the apparatus embodied by or otherwise associated with the reporting system, such as the processing circuitry, may again restructure the reporting template from the second order in which the sections of the reporting template were presented during generation of the report to the first order, such as the order predefined by the site, the practice or the like. As such, the resulting report having sections arranged in the first order will have the same organization as other reports so as to facilitate review of the report, even though the sections were differently arranged in the second order during the generation of the report so as to increase the efficiency with which the report can be generated.

Although the restructuring of the reporting template based upon the context of one or more images presented by the imaging system 10 constitutes an action taken by the reporting system 12 based upon data provided by the imaging system, the apparatus 20 embodied by or otherwise associated with the reporting system may also include means, such as the processing circuitry 12, for causing one or more other actions to be taken by the imaging system and/or the reporting system based upon data provided by the other one of the imaging system or the reporting system. Examples of these other actions that may be taken will be described below.

In this regard, various actions may be taken by the imaging system 10 and/or the reporting system 12 based upon data provided by the other one of the imaging system or the reporting system. In an embodiment in which the information relating to the context of one or more images presented by the imaging system that is transferred to the reporting system includes information regarding one or more comparison studies that are also presented by the imaging system, the reporting system and, more particularly, the apparatus 20 embodied by or otherwise associated with the reporting system, such as the processing circuitry 22, may cause an action to be taken by causing an indication of the one or more comparison studies maintained by the imaging system to be included within a section of the reporting template, such as in the section entitled "Comparison" as shown in FIG. 5. In this regard, the action taken by the reporting system of causing an indication of one or more comparison studies to be included within a section of the reporting template is based upon data provided by the imaging system that identifies the one or more comparison studies.

Figure 6:
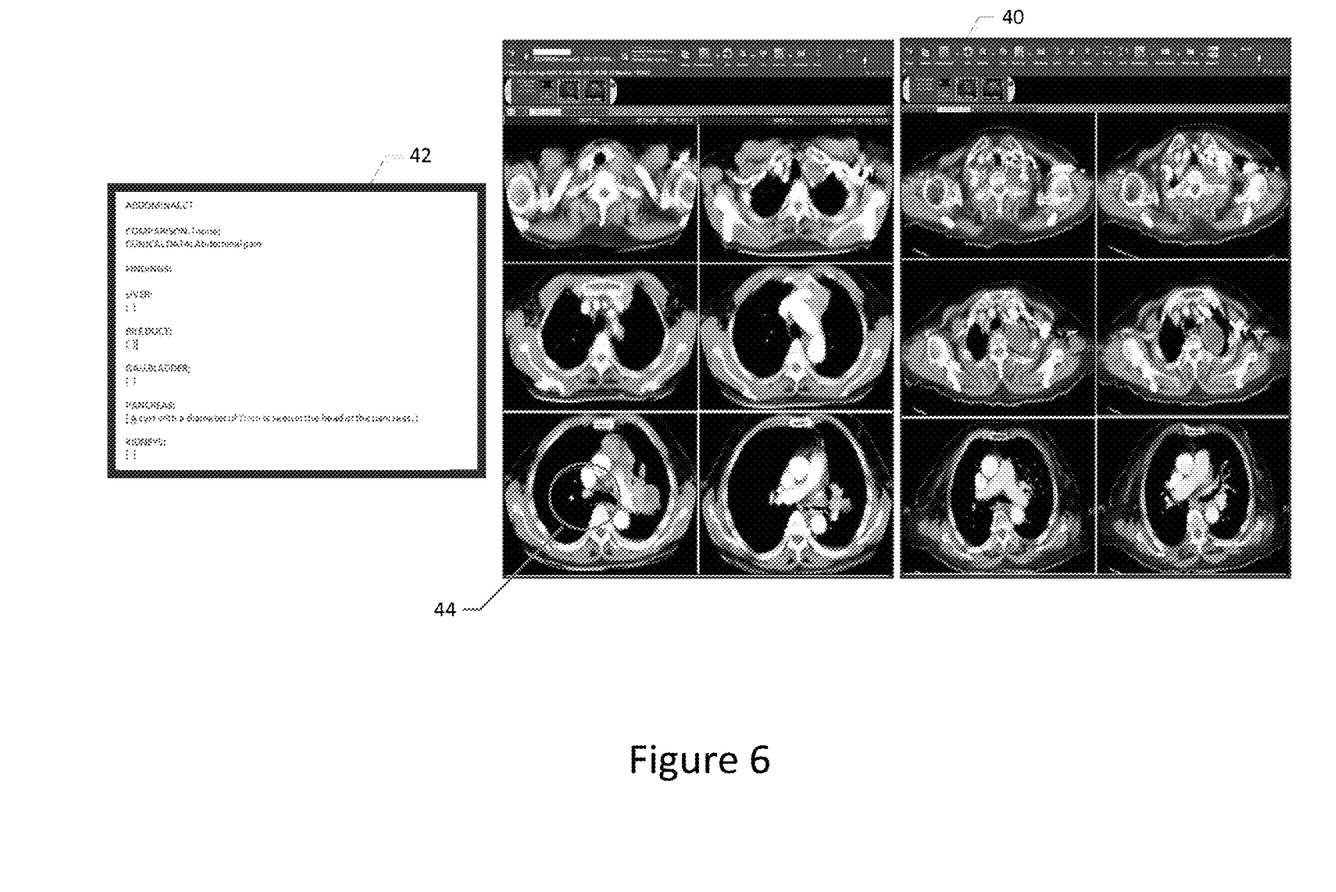
FIG. 6 depicts a plurality of images presented by an imaging system and a report template presented by a reporting system which is auto-populated by a measurement from the imaging system in accordance with an example embodiment of the present invention.

In some embodiments, a radiologist reviewing the images 40 presented by the imaging system 10 may identify a particular portion of an image, such as a cyst, an abnormality or the like. In response to the radiologist's selection of the particular portion of the image, the imaging system may determine a measurement of the selected portion of the image, such as the diameter, the length or the like. In accordance with an example embodiment, the imaging system may provide data relating to the measurement of the selected portion of the image to the reporting system 12. As such, the reporting system and, more particularly, the apparatus 20 embodied by or otherwise associated with the reporting system, such as the processing circuitry 22, may cause an action to be taken by causing a section of the reporting template 42 to be auto-populated with the measurement captured by the imaging system. As shown in FIG. 6, for example, a radiologist reviewing the images presented by the imaging system may identify a cyst on the pancreas as indicated by circle 44. The imaging system may, in turn, determine the diameter of the cyst to be 7 mm and may provide data defining the measurement of the cyst upon the pancreas to the reporting system which may, in turn, auto-populate the section of the reporting template relating to the pancreas with the measurement of the cyst as shown in FIG. 6.

Figure 7:
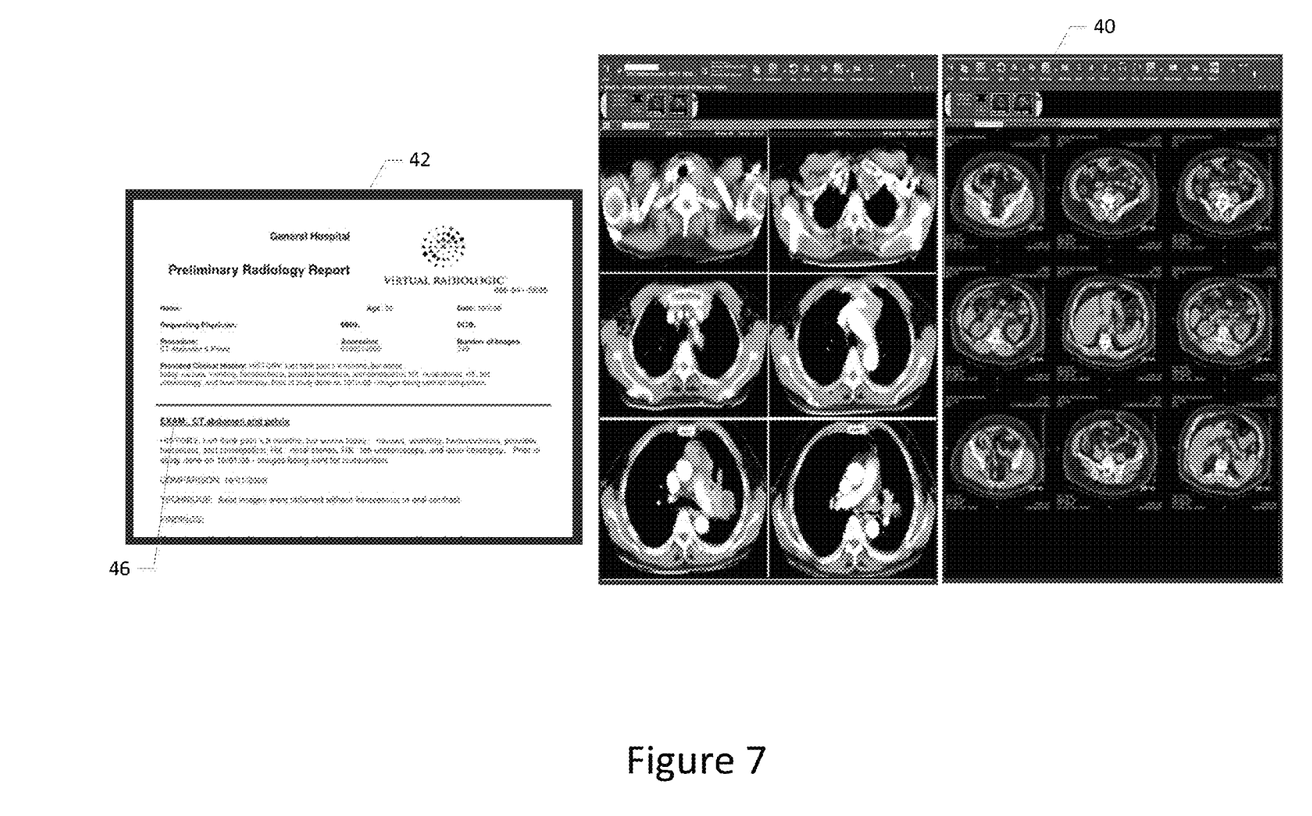
FIG. 7 depicts a report presented by a reporting system and including an actuable identifier to one or more images as well as the plurality of images presented by an imaging system that are associated with the actuable identifier in accordance with an example embodiment of the present invention.

In an example embodiment, the reporting system 12 and, more particularly, the apparatus 20 embodied by or otherwise associated with the reporting system, such as the processing circuitry 22, may cause an action to be taken by causing an actuable identifier, such as a hyperlink, a thumbnail or the like, to be included within a section of the reporting template 42. In this regard, the imaging system 10 may provide the reporting system with the data identifying the image study and/or a respective image that is presented by the imaging system. The reporting system, such as the processing circuitry may cause an actuable identifier, such as a hyperlink, to be inserted within a section of the reporting template that identifies the image study and/or a respective image that is presented by the imaging system based upon the data provided by the imaging system. In response to user actuation of the actuable identifier, the reporting system may cause the imaging system to present the image study and/or the respective image identified by the actuable identifier. In the example embodiment of FIG. 7, for example, the Preliminary Radiology Report may include a hyperlink 46 that identifies "EXAM: CT abdomen and pelvis". Actuation of this hyperlink may cause the imaging system to present the associated image study that formed the basis of the Preliminary Radiology Report. As such, a radiologist or other health care provider may quickly locate and view the images relating to or otherwise underlying a report that is of interest.

In another example embodiment, the imaging system 10 and, more particularly, the apparatus 20 embodied by or otherwise associated with the imaging system, such as the processing circuitry 22, may cause an action to be taken by causing an annotation to be associated with an image maintained by the imaging system. In this regard, the annotation is based upon data provided by the reporting system 12 to the imaging system and, in one embodiment, may include information identifying the report that has been generated based upon the associated image study and/or image as maintained by the imaging system. The imaging system, such as the processing circuitry, may associate the annotation with the image such that subsequent display of the image may also cause the annotation to be displayed in conjunction with the associated image. As such, a radiologist or other health care practicioner may quickly determine if a report has been prepared based upon an image so as to facilitate the efficient review of the report, if so desired.

Figure 8:
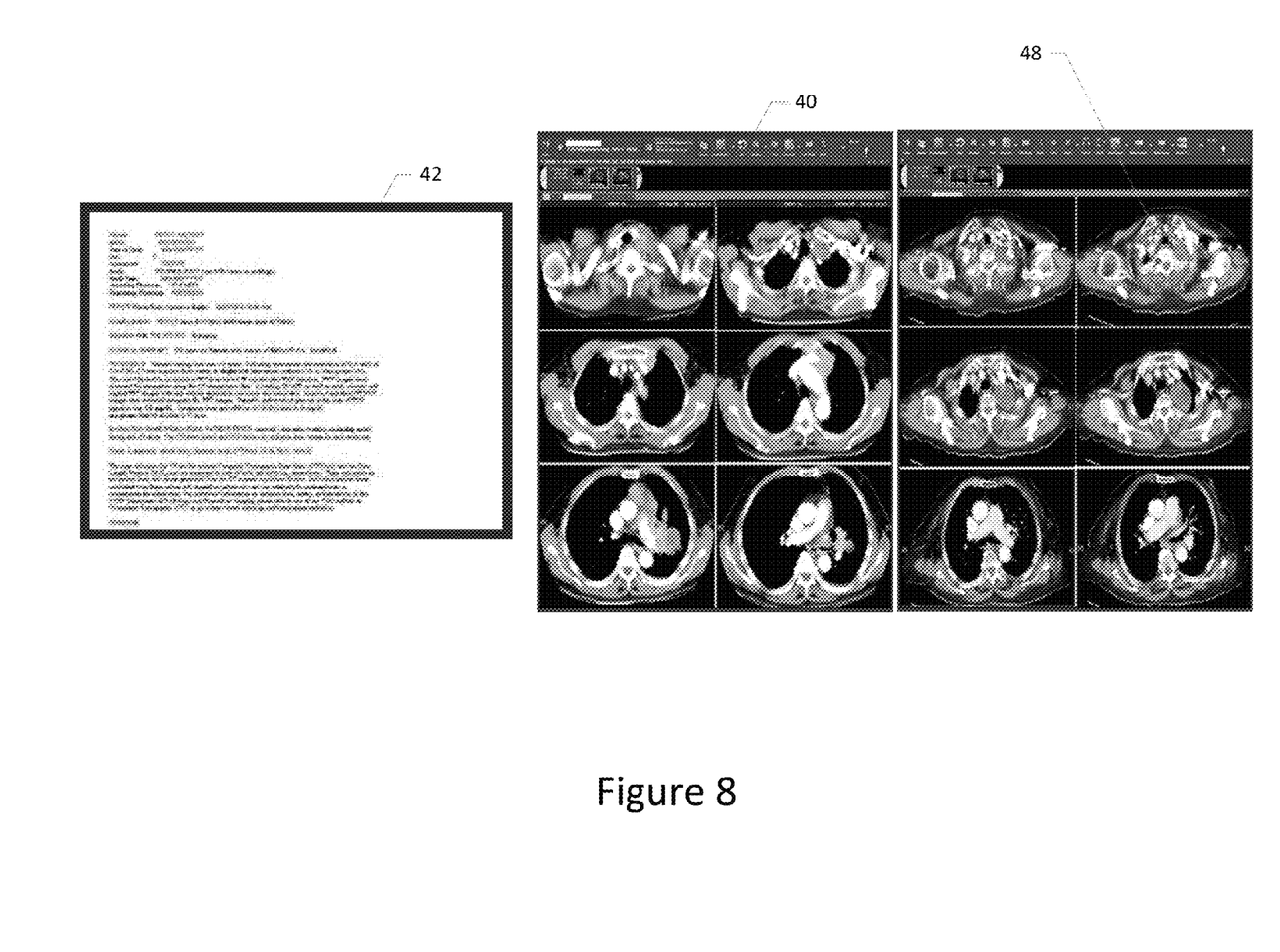
FIG. 8 depicts a plurality of images presented by an imaging system and including an annotation and a report associated with the annotation in accordance with an example embodiment of the present invention.

Various types of annotations may be associated with corresponding images. As shown in FIG. 8, for example, an image presented by the imaging system 10 may include an annotation 48, such as a dot, a circle or other visible indication, of a portion of interest of the image. In another embodiment, the annotation may identify the report that was generated based upon the associated image or the image study that includes the associated image. In this regard, the report may be identified by title, number or the like. As such, a radiologist or other health care provider reviewing the images may efficiently determine the existence of a report based upon the image and may, in turn, efficiently locate or access the report in order to review the report. In a further embodiment, the annotation may be an actuable identifier, such as a hyperlink or the like, that may be actuated by a radiologist or other health care provider who is reviewing the images to cause the corresponding report to be presented, such as upon an auxiliary display.

By way of example, a sample workflow for creating a radiology report based upon an abdominal CT image study will now be described. In this example, a radiologist may select the abdominal CT image study from the PACS study list and may launch the PACS viewer to view the images of the abdominal CT image study. In accordance with an example embodiment, information relating to the context of one or more images of the abdominal CT image study that are presented by the PACS viewer are transferred to the reporting system 12 and the reporting system restructures the reporting template to follow the same order as that defined by the display protocol in which the images presented by the PACS viewer are arranged. As such, the radiologist may complete the report efficiently without having to flip back and forth between different images of the image study in order to locate the image(s) of the region or organ of the body that corresponds to a respective section of the reporting template. In this example, the PACS viewer may also display one or more comparison studies including relevant prior images and may advise the reporting system of the one or more comparison studies such that information identifying the one or more comparison studies may be included in the appropriate section of the reporting template. The radiologist may then view the images in the sequence defined by the display protocol.

During the interpretation of the image study of this example workflow, the radiologist may identify an abnormal cyst on the pancreas. In accordance with an example embodiment, one or more prior reports for the patient may also be displayed, such as by the display of a listing of one or more prior reports. Alternatively, an image from the comparison study may include an annotation indicating the existence of a report based upon the comparison study. As such, the radiologist may select a prior report, such as from a prior abdominal CT image study, and may determine that the cyst was noted in the prior report as "requires follow-up". The radiologist may then select the hyperlink included in the prior report relating to the cyst which causes the prior CT image study that was utilized as a basis for the prior report to be launched by the imaging system 10. By reviewing the image of the cyst, the radiologist in this example may readily determine that the cyst has grown and the dimensions of the cyst have changed. The radiologist may then add information to the report, such as the pancreas section of the reporting template, indicating that the cystic mass has grown since the prior examination. As a result of the transfer of data from the imaging system to the reporting system 12, the pancreas section of the reporting template may be automatically populated with an identification of the prior comparison study and the measurements of the cyst as identified by the radiologist in the current image study. Once the radiologist has finalized the report, the reporting system 12 may automatically restructure the report so that the report no longer necessarily follows the order defined by the display protocol of the imaging system 10, but, instead, matches the first order defined by the health care facility, the practice, etc.

In this example, the report may be distributed to the primary care physician or other health care provider. The primary care physician may then meet with the patient to inform the patient of the findings and to discuss the next steps. While meeting with the patient, the primary care physician may access the report and, as a result of the order of the report being consistent with the first order of other reports of the health care facility or the physician's practice, the primary care physician is able to quickly navigate to the relevant section of the report as well as to display of the image study from which the report was generated. As indicated above, the section of the reporting template relating to the pancreas may include an indication of the comparison study from which the finding that the cyst has grown and changed in dimensions was determined. As such, the primary care physician may select the hyperlink associated with the comparison study that is included within the pancreas section of the reporting template in order to also launch the comparison study within the imaging system 10. The primary care physician is now able to visually show the patient that the dimensions of the cyst have changed without having to manually search for the studies in the imaging system and scroll through the images in the abdominal CT image study to locate the image in which the cyst was noted in both the current image study and the comparison study.

Continuing with this example, the primary care physician may refer the patient to a gastrointestinal surgeon for a biopsy of the pancreatic cyst. In preparation for the procedure, the surgeon may utilize the imaging system 10 to display the current and comparison images of the pancreas. In reviewing the current abdominal CT image study, the surgeon may observe a minute mass in the kidney. As the kidney may be outside of the area of expertise of the surgeon, the surgeon may not be able to readily identify the mass, but would like to ensure that the radiologist has considered the mass in the diagnosis. In accordance with an example embodiment, the image that depicts the kidney mass may be annotated so as to identify the corresponding report. In an instance in which the annotation is a hyperlink, the surgeon may select the hyperlink so as to cause the corresponding report to be displayed. In the report, the surgeon may learn that the mass was considered small and unremarkable and likely a minor calcification by the radiologist. As such, the surgeon may continue to focus on the planned biopsy for the pancreatic cyst in an efficient manner.

As described above, FIGS. 3 and 4 illustrates a flowchart of a system, method, and computer program product according to example embodiments of the invention. It will be understood that each block of the flowchart, and combinations of blocks in the flowchart, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may be stored by one or more memory devices of a computing system, e.g., a PACS in accordance with FIG. 3 and/or a reporting system in accordance with FIGS. 3 and 4, and executed by a processing circuitry 22 in the computing device. In some embodiments, the computer program instructions comprising the computer program product(s) which embody the procedures described above may be stored by memory devices of a plurality of computing devices. As will be appreciated, any such computer program product may be loaded onto a computer or other programmable apparatus to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product comprises an article of manufacture which implements the function specified in the flowchart block(s). The computer program instructions of one or more computer program products may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks or steps of the flowchart support combinations of means for performing the specified functions and combinations of steps for performing the specified functions. It will also be understood that one or more blocks of the flowchart, and combinations of blocks in the flowchart, may be implemented by special purpose hardware-based computer systems which perform the specified functions or steps, or combinations of special purpose hardware and computer program product(s).

The above described functions may be carried out in many ways. For example, any suitable means for carrying out each of the functions described above may be employed to carry out embodiments of the invention. In one embodiment, a suitably configured processing circuitry 22 may provide all or a portion of the elements of the invention. In another embodiment, all or a portion of the elements of the invention may be configured by and operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

Many modifications and other embodiments of the inventions set forth herein will come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method of providing an interface between an imaging system and a reporting system, the method comprising:
participating in a transfer of information relating to a context of one or more images presented by the imaging system to cause a reporting template to be restructured based upon the context of one or more images presented by the imaging system, wherein the information relating to a context of one or more images comprises a display protocol relating to an order in which the one or more images are presented by the imaging system;
causing, with a processor, an action to be taken in one of the imaging system or the reporting system based upon data provided by another of the imaging system or the reporting system, wherein causing an action to be taken comprises restructuring the reporting template from a reporting template having a first order to a reporting template having a second order based upon the context of one or more images presented by the imaging system;
generating a report including information relating to the one or more images that is received while the reporting template has the second order; and
following generation of the report, restructuring the reporting template that defines an ordering of sections of the report into which the information relating to the one or more images was entered during generation of the report from the second order in which the sections of the reporting template were presented during generation of the report to the first order.

2. A method according to claim 1 wherein participating in the transfer of information comprises receiving information relating to the context of one or more images presented by the imaging system.

3. A method according to claim 1 wherein causing an action to be taken comprises causing a section of the reporting template to be auto-populated with a measurement captured with the imaging system.

4. A method according to claim 1 wherein causing an action to be taken comprises causing an indication of one or more comparison studies maintained by the imaging system to be included within a section of the reporting template.

5. A method according to claim 1 wherein causing an action to be taken comprises causing an actuable identifier to an image maintained by the imaging system to be included within a section of the reporting template.

6. A method according to claim 1 wherein causing an action to be taken comprises causing an annotation to be associated with an image maintained by the imaging system.

7. A computing system for providing an interface between an imaging system and a reporting system, the computing system comprising a processor configured to:
participate in a transfer of information relating to a context of one or more images presented by the imaging system to cause a reporting template to be restructured based upon the context of one or more images presented by the imaging system, wherein the information relating to a context of one or more images comprises a display protocol relating to an order in which the one or more images are presented by the imaging system;
cause an action to be taken in one of the imaging system or the reporting system based upon data provided by another of the imaging system or the reporting system, wherein the action is caused to be taken by restructuring the reporting template from a reporting template having a first order to a reporting template having a second order based upon the context of one or more images presented by the imaging system;
generate a report including information relating to the one or more images that is received while the reporting template has the second order; and
following generation of the report, restructure the reporting template that defines an ordering of sections of the report into which the information relating to the one or more images was entered during generation of the report from the second order in which the sections of the reporting template were presented during generation of the report to the first order.

8. A computing system according to claim 7 wherein the processor is configured to participate in the transfer of information by receiving information relating to the context of one or more images presented by the imaging system.

9. A computing system according to claim 7 wherein the processor is configured to cause an action to be taken by causing a section of the reporting template to be auto-populated with a measurement captured with the imaging system.

10. A computing system according to claim 7 wherein the processor is configured to cause an action to be taken by causing an indication of one or more comparison studies maintained by the imaging system to be included within a section of the reporting template.

11. A computing system according to claim 7 wherein the processor is configured to cause an action to be taken by causing an actuable identifier to an image maintained by the imaging system to be included within a section of the reporting template.

12. A computing system according to claim 7 wherein the processor is configured to cause an action to be taken by causing an annotation to be associated with an image maintained by the imaging system.

13. A computer program product for providing an interface between an imaging system and a reporting system, the computer program product comprising a non-transitory computer-readable storage medium having computer-executable program code portions stored therein, the computer-executable program code portions comprising program code instructions for:
participating in a transfer of information relating to a context of one or more images presented by the imaging system to cause a reporting template to be restructured based upon the context of one or more images presented by the imaging system, wherein the information relating to a context of one or more images comprises a display protocol relating to an order in which the one or more images are presented by the imaging system;
causing an action to be taken in one of the imaging system or the reporting system based upon data provided by another of the imaging system or the reporting system, wherein causing an action to be taken comprises restructuring the reporting template from a reporting template having a first order to a reporting template having a second order based upon the context of one or more images presented by the imaging system;
generating a report including information relating to the one or more images that is received while the reporting template has the second order; and
following generation of the report, restructuring the reporting template that defines an ordering of sections of the report into which the information relating to the one or more images was entered during generation of the report from the second order in which the sections of the reporting template were presented during generation of the report to the first order.

14. A computer program product according to claim 13 wherein the program code instructions for participating in the transfer of information comprise program code instructions for receiving information relating to the context of one or more images presented by the imaging system.

15. A computer program product according to claim 13 wherein the program code instructions for causing an action to be taken comprise program code instructions for causing a section of the reporting template to be auto-populated with a measurement captured with the imaging system.

16. A computer program product according to claim 13 wherein the program code instructions for causing an action to be taken comprise program code instructions for causing an actuable identifier to an image maintained by the imaging system to be included within a section of the reporting template.

17. A computer program product according to claim 13 wherein the program code instructions for causing an action to be taken comprise program code instructions for causing an annotation to be associated with an image maintained by the imaging system.

18. A method according to claim 1 wherein the first order of the reporting template is defined by a healthcare facility or a healthcare practice.

19. A computing system according to claim 7 wherein the first order of the reporting template is defined by a healthcare facility or a healthcare practice.

20. A computer program product according to claim 13 wherein the first order of the reporting template is defined by a healthcare facility or a healthcare practice.

* * * * *

UNITED STATES PATENT AND TRADEMARK OFFICE
CERTIFICATE OF CORRECTION

PATENT NO.        : 9,292,655 B2
APPLICATION NO.   : 13/953216
DATED             : March 22, 2016
INVENTOR(S)       : Arazi et al.

It is certified that error appears in the above-identified patent and that said Letters Patent is hereby corrected as shown below:

In the claims:

Column 15,
Line 19, "template having" should read --template having a--.

Signed and Sealed this
Fourteenth Day of June, 2016

Michelle K. Lee
*Director of the United States Patent and Trademark Office*